United States Patent [19]

Roberts

[11] Patent Number: 5,580,567
[45] Date of Patent: *Dec. 3, 1996

[54] HOMOGENEOUS, ESSENTIALLY NONAQUEOUS ADJUVANT COMPOSITIONS WITH BUFFERING CAPABILITY

[75] Inventor: Johnnie R. Roberts, Memphis, Tenn.

[73] Assignee: Helena Chemical Company, Memphis, Tenn.

[*] Notice: The term of this patent shall not extend beyond the expiration date of Pat. No. 5,178,795.

[21] Appl. No.: 394,839

[22] Filed: Feb. 27, 1995

Related U.S. Application Data

[63] Continuation-in-part of Ser. No. 960,894, Oct. 14, 1992, Pat. No. 5,393,791, and Ser. No. 554,359, Jul. 19, 1990, Pat. No. 5,178,795.

[51] Int. Cl.$^6$ .......................... A01N 25/02; A01N 27/00; B01J 13/00
[52] U.S. Cl. .......................... 424/405; 71/DIG.1; 252/312; 252/356; 514/762; 514/941
[58] Field of Search .......................... 252/321, 356, 252/DIG.1; 514/762, 94.1; 71/DIG. 1; 510/437; 424/405

[56] References Cited

U.S. PATENT DOCUMENTS

| | | | |
|---|---|---|---|
| 2,380,166 | 7/1945 | Griffin | 252/312 X |
| 2,528,136 | 10/1950 | Goldstein et al. | 252/356 |
| 3,071,550 | 1/1963 | Altscher et al. | 252/354 |
| 3,894,149 | 7/1975 | Mast | 71/DIG. 1 |
| 3,898,075 | 8/1975 | Freund et al. | 71/DIG. 1 |
| 3,997,322 | 12/1976 | Ratledge | 504/225 |
| 4,097,403 | 6/1978 | Tsutsumi et al. | 252/DIG. 1 |
| 4,224,049 | 9/1980 | Devisetty et al. | 71/DIG. 1 |
| 4,313,847 | 2/1982 | Chasin et al. | 252/356 |
| 4,637,830 | 1/1987 | Dyer et al. | 71/DIG. 1 |
| 4,755,207 | 7/1988 | Bannon | 71/DIG. 1 |
| 4,834,908 | 5/1989 | Hazen et al. | 252/356 |
| 4,851,421 | 7/1989 | Iwasaki et al. | 514/941 X |
| 4,944,949 | 7/1990 | Story et al. | 514/914 X |
| 4,966,728 | 10/1990 | Hazen | 252/356 X |
| 5,178,795 | 1/1993 | Roberts | 252/356 |
| 5,206,021 | 4/1993 | Dookhith et al. | 424/405 |
| 5,393,791 | 2/1995 | Roberts | 514/762 |

FOREIGN PATENT DOCUMENTS 703607  2/1965  Canada .............................. 71/DIG. 1

OTHER PUBLICATIONS

Rose et al.: *The Condensed Chemical Dictionary*, Sixth Edition, Reinhold Publishing Corp., New York (1961), p. 858.

Simanton et al.: "Recommended Specifications for Citrus Spray Oils in Florida", Reprint from vol. 79 of Proceedings of the Florida State Horticultural Society, Miami, Oct. 24–27, 1966, pp. 26–30.

Primary Examiner—Richard D. Lovering
Attorney, Agent, or Firm—Connolly & Hutz

[57] ABSTRACT

A homogeneous, essentially nonaqueous adjuvant composition containing at least one spray oil selected from the group consisting of
(a) vegetable oils;
(b) fatty acids and blends thereof;
(c) esterified fatty acids or blends thereof;
(d) saponified fatty acids or blends thereof;
(e) N,N-dimethylamide of the formula $RCON(CH_3)_2$ (f) polybutenes of the following formula

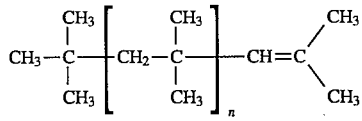

a surfactant in an effective amount to emulsify said composition and a buffering agent in amount sufficient to reduce the pH to below about 7.

30 Claims, No Drawings

HOMOGENEOUS, ESSENTIALLY NONAQUEOUS ADJUVANT COMPOSITIONS WITH BUFFERING CAPABILITY

CROSS REFERENCE TO RELATED APPLICATION

This application is a continuation-in-part of Ser. No. 07/960,894, which was filed Oct. 14, 1992 and is now issued as U.S. Pat. No. 5,393,791 and a continuation-in-part of Ser. No. 07/554,359, which was filed Jul. 19, 1990 and is now issued as U.S. Pat. No. 5,178,795.

The present invention relates to the field of agricultural, forestry, turf, ornamental, industrial, aquatic, rights-of-ways and other applications where pesticides are used and, more specifically, to adjuvant compositions which improve the chemical and physical properties of a pesticide such as an herbicide, insecticide or fungicide.

BACKGROUND OF THE INVENTION

In order to enhance or modify the chemical and/or physical characteristics of certain pesticides, certain materials are added to form a mixture for spraying. Generally referred to as adjuvants, these materials have no pesticidal activity of their own. Since spray application can be critical to the performance of the agricultural chemical, adjuvants are added to reduce application problems such as chemical stability, incompatibility, solubility, suspension, foaming, drift, evaporation, volatilization, phytotoxicity, surface tension, droplet size and coverage. They can, depending on their type, enhance wetting, spreading, sticking, emulsifying, dispersing and biological activity. Adjuvants include wetting agents, crop oil concentrates, spreaders, stickers, buffering agents, foaming and anti-foaming agents, dispersing agents and drift control agents. Over 200 EPA-registered pesticides have specific recommendations on their labels for adjuvant use. These are recommended for one of two reasons—or both. First, to enhance biological activity of the pesticide and second, to reduce, minimize or eliminate spray application problems as noted previously. There are several different types of adjuvants recommended. To achieve consistent, effective results from them, the user must first select the desired type of adjuvant and then the appropriate product within that specific type for use with a particular pesticide and then use that product at recommended rates.

It is known that petroleum hydrocarbon spray oils increase the efficacy of herbicides, fungicides and other pesticides by enhancing the deposition characteristics and wetting and spreading of the spray solution resulting in a more even and uniform spray deposit or by increasing the biological effect of certain pesticides. Other oils such as esterified vegetable oils and once—refined vegetable oils are known to exhibit similar properties. Such spray oils can increase penetration and slow evaporation. Paraffin based spray oil is a petroleum oil used as dormant spray, summer oil, carrier for pesticides or an adjuvant to increase the efficacy of agricultural chemicals.

In U.S. Pat. No. 3,977,322, an agricultural spray oil composition comprising a major Mount of a petroleum oil and a minor amount of a vegetable oil is disclosed as providing a particularly improved carrier which enhances the effectiveness of selective herbicides.

A synergistic herbicidal composition is disclosed in U.S. Pat. No. 4,755,207 and comprises a non-phytotoxic crop oil, a surfactant, and hydrophobic mycoherbicide spore. The oils are once refined vegetable oils or highly refined paraffinic material. The surfactant can be anionic, cationic or nonionic.

A surfactant composition is disclosed in U.S. Pat. No. 4,317,847 issued to Chasin. Chasin discloses a solvent having a high aromatic content above 95% which corresponds to a very low UR value.

Some applications require the separate addition of buffering agents to adjust the pH of alkaline waters used to make up the spray solutions. The buffering agents regulate solution pH to avoid hydrolysis of pesticides that tend to decompose in alkaline spray solutions. Generally, the spray's pH should be adjusted to a range of 4 to 6 or slightly acidic. Known buffering agents include alkyl aryl polyethoxy ethanol phosphates and organic phosphatic acids as the principal functioning agents. Typically, such a buffering agent is added to the water which is then combined with the pesticide and any other adjuvants required.

U.S. Pat. No. 4,244,049 relates to aqueous-lower alkanol solutions containing alkylaryl polyoxyethylene glycol phosphate esters which act as compatibility agents for mixtures of liquid fertilizer and pesticides. The solution contains about 20% methanol, about 16% water and about 64% of the phosphate ester.

A biocidal fine powder and an agricultural suspension containing the fine powder and an adjuvant are disclosed in U.S. Pat. No. 4,851,421. The adjuvant can be a polyoxyalkylene-type nonionic surface active agent or polyoxyalkylene alkyl or alkylaryl ether phosphates or their salts. The composition does not include any oil components.

It is advantageous to reduce the separate addition of each of the adjuvants to the herbicide or pesticide to save time and to reduce possibility of error in the amounts added since mixing is typically done in the field by unskilled workers. However, the components of an adjuvant composition must form a homogeneous liquid mixture, not a slurry or suspension. Otherwise, the amount of oil and surfactant in the spray will vary form use to use and these variations would adversely affect the physical properties of the spray. In the prior compositions, adjuvants such as buffering agents have been added to the water, then combined with the other adjuvants and the active ingredient because the phosphate compounds used as buffering agents are hydrophilic polar compounds. It is difficult to combine such compounds with oil and obtain a homogeneous composition having the desired spray uniformity and coverage.

It is the object of this invention to provide an essentially non-aqueous, single-phase adjuvant composition containing oil plus surfactant blend and which provides buffering capability. Even after the addition of alkaline water and pesticides, use of this composition reduces and/or maintains the pH of the spray mixture within a desired range to prevent hydrolysis of the pesticide.

SUMMARY OF THE INVENTION

The present invention is a homogeneous, essentially non-aqueous adjuvant composition comprising a spray oil, a surfactant and a buffering agent in an amount to reduce the pH to below about 7. When mixed with a pesticide, the composition provides one-step addition of the adjuvants to obtain a more uniform spread of the spray solution of the herbicide or pesticide, improved penetration and slower evaporation. The adjuvant can also be used as a pesticide or herbicide without the addition of any additional pesticide to the adjuvant. The presence of the buffering agent maintains the pH of the mixture within a desired range pH below about 7 in the presence of alkaline waters typically used in spray solutions.

DETAILED DESCRIPTION OF THE INVENTION

This invention is a homogeneous, essentially nonaqueous adjuvant composition having buffering capability. According to the process of this invention, the adjuvant composition comprises a spray oil and a blend of surfactants and buffering agent. The preferred homogeneous, essentially nonaqueous adjuvant composition comprises:

(1) at least one spray oil selected from the group consisting of:
  (a) vegetable oils;
  (b) fatty acids and blends thereof;
  (c) esterified fatty acids or blends thereof;
  (d) saponified fatty acids or blends thereof;
  (e) N,N-dimethylamide of the formula

wherein R is an alkyl chain derived from fatty acids having about 6 to about 18 carbon atoms;
  (f) polybutenes of the following formula

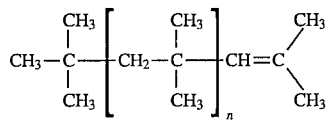

where n is a number from about 1 to about 50%
(2) a surfactant in an effective amount to provide emulsification of said composition and
(3) a buffering agent in an amount sufficient to reduce the pH to below about 7.

The spray oils utilized in this composition do not have an unsulfonated residence (UR) value and include at least one of the following:

1. Vegetable oils:
   the vegetable oils can be, but are not limited to vegetable seed oil or a mixture of vegetable seed oils, as they are known in the agricultural industry, crop seed oils which are produced from the particular crop from which their name is derived. Included in the vegetable oils suitable for the compositions of the present invention are cotton seed oil, canola, rapeseed, peanut oil, sunflower oil, linseed oil, safflower oil, soybean oil, corn oil, olive oil, coconut oil, tall oil or other seed oils and blends of the above oils such as cotton seed oil plus soybean oil; cotton seed oil plus peanut oil; cotton seed oil plus olive oil; corn oil plus linseed oil; corn oil plus soybean oil; as well as blends of any two or more of the above disclosed vegetable oils. The vegetable oils can be present in an amount from about 1 to about 99%, preferably from about 50 to about 99% and most preferably from about 80 to about 99%.

2. Fatty acids and blends thereof:
   Such as, but not limited to saturated and unsaturated fatty acids of about 6 to about 18 carbon atoms. The fatty acids and blends can be present in an amount from about 1 to about 99%, preferably from about 50 to about 99% and most preferably from about 80 to about 99%.

3. Esterified fatty acids or blends thereof:
   Such as, but not limited to saturated and unsaturated esters of about 6 to about 18 carbon atoms. The esterified fatty acids can be present in an amount from about 1 to about 99%, preferably from about 50 to about 99% and most preferably from about 50 to about 80%. The esterified fatty acids may also be derived from any of the vegetable oils previously mentioned.

4. Saponified fatty acids or blends thereof:
   Such as, but not limited to saturated and unsaturated soaps of about 6 to about 18 carbon atoms. The saponified fatty acids can be present in an amount from about 1 to about 99%, preferably from about 50 to about 99% and most preferably from about 50 to about 80%. The saponified fatty acids may also be derived from any of the vegetable oils previously mentioned. N,N dimethylamides of the following formula:

wherein R is an alkyl chain derived from fatty acids having about 6 to about 18 carbon atoms. The N,N dimethylamides can be present in an amount from about 1 to about 99%, preferably from about 50 to about 99% and most preferably from about 80 to about 99 %.

6. Polybutenes:
   The polybutenes that can be used are of the following formula:

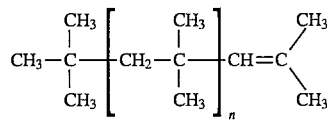

where n is a number from about 1 to about 50. The polybutenes can be present in an amount from about 1 to about 99%, preferably from about 50 to about 99% and most preferably from about 80 to about 99%.

7. Mixture of at least one of 1–6 above.

These 6 groups of oils can be a portion of the spray oil or the entire spray oil.

The spray oil is used in combination with one or more of the buffering agents and should be mixed with one or more of the surfactants below. The surfactant is present in an effective amount to provide emulsification of the composition. The amount of the surfactant is usually in the range of about 5.0 to about 19.5% by weight. The preferred blend of surfactants include but are not limited to
a) sorbitan fatty acid ester,
b) polyethoxylated derivative of a sorbitan fatty acid ester,
c) fatty alkanolamides of the formula

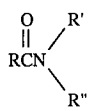

wherein R is an alkyl group having about 6 to about 25 carbon atoms; R and R" independently of one another are selected from the group consisting of hydrogen, —CH₂CH₂OH or $$CH_2-CH-OH$$
$$|$$
$$CH_3$$

d) PEG esters of the formula $$RC-(CH_2CH_2O)_mR'$$
$$\|$$
$$O$$

wherein R is a fatty alkyl having from about 2 to about 25 carbon atoms, R' is a fatty alkyl having from about 2 to about 25 carbon atoms or H and m is a number from 1 to about 100,
e) silicone surfactants of the formula $$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_x-\left[\underset{\underset{(CH_2)_n}{|}}{\overset{\overset{CH_3}{|}}{Si}}-O\right]_y-\underset{\underset{CH_3}{|}}{\overset{\overset{CH_3}{|}}{Si}}-CH_3$$
$$|$$
$$O$$
$$|$$
$$(C_2H_4O)_a(C_3H_6O)_bR$$

wherein R and R' independently from one another are alkyl having from 1 to about 20 carbon atoms, x is a number from 0 to about 5, y is a number from about 1 to about 5, a is a number from about 3 to about 25, b is a number from about 0 to about 25, n is a number from about 2 to about 4 and R is H, an alkyl group having 1 to 4 carbon atoms or an alkyl ester group having 1 to 4 carbon atoms,
f) ethoxylated fatty acids $$O$$
$$\|$$
$$RC-O-(CH_2CH_2O)_nH$$

wherein R is an alkyl group having from about 6 to about 25 carbon atoms, n is a number from 1 to about 100,
g) alkyl ethoxylates $$RO(CH_2CH_2O)_xH$$

wherein R is an alkyl group having from about 1 to about 50 carbon atoms and x is a number from 1 to about 100,
h) alkylphenol ethoxylates R—⟨phenyl⟩—(OCH₂CH₂)ₙOH
         |
         R' wherein R is H or an alkyl having from about 1 to about 20 carbons. R' is H or an alkyl having from about 1 to about 20 carbons and n is a number from 1 to about 100,
i) polypropylene glycols $$HO-(CH-CH_2-O)_{(n-1)}-CH_2-CH-OH$$
$$\ \ \ |\ \ \ \ \ \ \ \ \ \ \ \ \ \ \ \ \ \ \ \ \ \ \ \ \ \ \ \ \ \ \ \ \ \ |$$
$$\ \ \ CH_3\ \ \ \ \ \ \ \ \ \ \ \ \ \ \ \ \ \ \ \ \ \ \ CH_3$$

wherein n is a number from 1 to about 100, j) tristyrylphenol alkoxylates or amine ethoxylates $$R-N\underset{(CH_2CH_2O)_yH}{\overset{(CH_2CH_2O)_xH}{\diagup}}$$

wherein x and y independently of one another are a number from about 1 to about 100 and R is an alkyl having from 1 to about 25 carbon atoms.

The preferred buffering agent are used at about 0.5 to about 10% by weight in the formulation. The amount will be determined by the ability of the composition to reduce pH values of the pesticide spray mix to about 7 or less. The most preferred would be one in which the pH reduction could be accomplished by using no more than 0.5% by volume of the final composition.

The preferred buffering agents include but are not limited to
a) alkylaryl polyethoxy phosphate ester,
b) $C_1$–$C_6$ carboxylic acids,
c) $C_1$–$C_6$ dicarboxylic acids,
d) phosphoric acid,
e) citric acid,
f) glutaric acid,
g) gluconic acid,
h) lactic acid,
i) glycolic acid,
j) acrylic acid,
k) carboxylated alcohol ethoxylate, preferably of the formula $$R-O(CH_2CH_2O)_xH$$

R is a carboxylic acid having from 1 to about 25 carbon atoms and x is from 1 to about 20 moles ethylene oxide,
l) ethoxylated alkylaryl phosphate esters;
m) ethoxylated alkylphenol carboxylate esters;
n) tristyrylphenol alkoxylate phosphate esters; and
o) tristyrylphenol alkoxylate carboxylate esters.

Additionally the spray oil used in the compositions of this invention can also contain agricultural spray oils which are petroleum hydrocarbon oil. The hydrocarbon oil is not required to be used in this invention. These spray oils are the refined fraction of petroleum oil and the preferred petroleum oil is a paraffin oil which is a blend of $C_{10}$–$C_{18}$ saturated aliphatic hydrocarbons. Spray oils can be characterized by specifications such as unsulfonated residue, API-gravity, distillation range and pour point. A high unsulfonated residue (UR) indicates a minimum of reactive material in the spray oil and the oil's degree of refinement. This UR value corresponds to about 100% minus the aromatic content. Kerosine, coal oil, naphtha and diesel fuel are all phytotoxic and exhibit low UR values due to their reactivity and therefore, they all have a high aromatic content. Paraffinic oils that have high UR values exhibit little or no phytotoxicity. A minimum of 92% UR is typically required for agricultural spray oils. A spray oil with a 31–34 API gravity indicates a high degree of paraffinic oil content. An API gravity value of 23 or less indicates an oil with aromatic and napthenic constituents. As a result, such oils are more reactive and phytotoxic. The distillation range determines physical properties of spray oils. Also, a high boiling range is an indication of an oil's phytotoxicity. Lower boiling ranges indicate that the oil has an increased evaporation rate and lower tenacity.

Agricultural spray oils useful in the compositions of this invention have distillation ranges between about 400 to about 500° F. Pour point values reflect the wax content of spray oils. A high value indicates a large amount of wax in the oil. Waxes reduce the spreading and penetration properties of the spray oil. The spray oils used in the present invention have pour points no greater than about 20° F. Generally, oils having a distillation range of 400°–435° F. are used in adjuvants for fungicide and pesticide applications. Oils having a distillation range of about 445° to about 500° F. are employed in adjuvants applications directed at herbicides. As noted previously, the higher boiling oils have increased phytotoxicity which is useful when the objective is to enhance the effectiveness of some contact-type herbicides.

The following table illustrates typical specifications of spray oils useful in the compositions of this invention.

| | | | | |
|---|---|---|---|---|
| Gravity API | 32.8 | 34.3 | 34.6 | 33.0 |
| Density | 0.8608 | 0.8530 | 0.8515 | 0.8597 |
| Unsulfonated Residue % | 99.0 | 99.0 | 99.0 | 93–97 |
| Pour Point °F. Max | −5 | −5 | −5 | −5 |
| Distillation D1160 °F. at 10 MM HG | | | | |
| 50% Recovered | 404 | 435 | 454 | 465–471 |
| Range 10–90% | 55 | 72 | 80 | |
| Viscosity CST C40° C. | 10.7 | 13.59 | 14.8 | 21.4 |
| SUS 100° F. | 60 | 70 | 82 | 112 |
| Flash °F. | 335 | 345 | 376 | 385 |
| Color | L0.5 | L0.5 | L0.5 | L0.5 |
| Pounds Per Gal. | 7.171 | 7.106 | 7.119 | 7.162 |

The adjuvant composition of this invention is useful with a broad range of pesticides where an oil concentration adjuvant is recommended. If applied properly, these adjuvant compositions can be used with fertilizer products and herbicides. Optimum applications and effects can be influenced by the crop, pest, spray equipment, spray volume, pressure, droplet size, spray mixture, environmental factors and other factors, Consequently, observation of the spray deposit is typically made and the adjuvant concentrations are adjusted accordingly. In mixing the adjuvant compositions with the pesticide or herbicide, the spray tank is filled one-half full with water and agitated. The pesticide and/or fertilizer is added as directed by labeling or in the following sequence: dry flowables or water dispersible granules, wettable powders, flowables, solutions and emulsifiable concentrates. The filling of the tank with water is continued and the adjuvant composition is added last and agitation is continued.

The pesticide or herbicide compositions containing the adjuvant compositions of the present invention can be applied by ground, aerial or aquatic spray equipment. In most cases, enough of the composition is applied to allow for adjustment of the spray pH to the desired range and uniform wetting and deposition of the spray on the leaf surfaces without undue runoff. For ground application, about 1 to about 4 pints are used in about 20 to about 100 gallons of spray solution per acre. Concentration should not exceed about 1.5% v/v. For low volume aerial application, about 2 to about 8 fl. oz. per acre are typically used. In an aquatic application, about 1 to about 4 pints per acre are used not to exceed about 1.5% v/v concentration.

EXAMPLES

Example 1

A mixture of 50.0 parts methyl ester of soybean oil and 30.0 parts of a polyethoxylated isodecyl alcohol phosphate ester and 20.0 parts of a nonylphenol with 6 moles of ethylene oxide was stirred until the mixture was homogeneous.

At the conclusion of blending, the mixture was clear and free of turbidity. The resultant mixture (Composition 1) had the following components:

| Chemical Name | % | Function |
|---|---|---|
| Methyl esters of soybean oil | 50.0 | Pesticide Activity Enhancement |
| Polyethoxylated isodecyl alcohol phosphate ester | 30.0 | Buffering agent |
| Nonylphenol with 6 moles of ethylene oxide (EO) | 20.0 | Emulsifier |
| TOTAL | 100.0 | |

A composition (Composition A) having the composition shown below is prepared to show the need to use the phosphate ester to obtain the advantages produced by the adjuvant compositions of the present invention.

| Chemical Name | % | Function |
|---|---|---|
| Methyl esters of soybean oil | 80.0 | Pesticide Activity Enhancement |
| Nonylphenol with 6 moles of ethylene oxide | 20.0 | Emulsifier |
| TOTAL | 100.0 | |

The following comparison shows that when the phosphate ester is omitted, the performance of the above composition as a buffering agent is inferior to the performance of the adjuvant compositions of the present invention. The compositions are added to distilled water at the rate of 0.5% by volume. Each mixture with water is then agitated to ensure complete dispersion of the emulsified oil in water. These mixtures are then titrated with a 10% diethanolamine solution. The pH is monitored after additions of the diethanolamine titrant.

| Composition with phosphate ester | | Composition without phosphate ester | |
|---|---|---|---|
| % volume titrant | pH | % volume titrant | pH |
| 0 | 2.1 | 0 | 6.8 |
| 0.75 | 5.1 | 0.75 | 9.0 |
| 0.90 | 6.0 | 0.90 | 9.2 |
| 1.50 | 8.0 | 1.50 | 9.5 |

Without the phosphate ester, the composition does not reduce the pH to the desired range of 4–6. Furthermore, addition of an alkaline material to the mixture raises the pH of the mixture without the phosphate ester much more readily.

Furthermore, the composition without the emulsifier produces an oil-in-water emulsion which begins to produce creamy separation after only 1 hour. The phosphate ester produced a mini-emulsion which is stable for over 24 hours.

Further Examples of the Patented Composition

| | | | |
|---|---|---|---|
| (2) | Saponified soybean oil | | 80.0% |
| | Nonylphenol with 6 moles EO | | 16.0% |
| | Acetic Acid | | 2.0% |

-continued

| | | |
|---|---|---|
| (3) | Polybutenes with an average molecular weight of 320 | 80.0% |
| | Nonylphenol with 6 moles EO | 18.0% |
| | Acetic Acid | 2.0% |
| (4) | Soybean oil | 80.0% |
| | Nonylphenol with 6 moles EO | 18.0% |
| | Acetic Acid | 2.0% |
| (5) | Oleic acid | 83.0% |
| | C10–12 alcohol with 6 moles EO | 15.0% |
| | Acetic Acid | 1.0% |
| | Lactic Acid | 1.0% |
| (6) | Methyl esters of soybean oil | 80.0% |
| | Nonylphenol with 6 moles EO | 10.0% |
| | Carboxylic acid ester of nonylphenol with 6 moles EO | 6.0% |
| | Acetic Acid | 2.0% |
| (7) | Methyl esters of soybean oil | 80.0% |
| | Nonylphenol with 6 moles EO | 10.0% |
| | Carboxylic acid ester of nonylphenol with 6 moles EO | 5.0% |
| | Acetic Acid | 2.0% |
| | Polyalkyleneoxide Modified heptametyltrisiloxane | 3.0% |

While there is shown and described herein certain specific structure embodying the invention, it will be manifest to those skilled in the art that various modifications and rearrangements of the parts maybe made without departing from the spirit and scope of the underlying inventive concept and that the same is not limited to the particular forms herein shown and described.

I claim:

1. A homogeneous, essentially nonaqueous adjuvant composition comprising at least one spray oil selected from the group consisting of:

(a) vegetable oils;
(b) fatty acids and blends thereof;
(c) esterified fatty acids or blends thereof;
(d) saponified fatty acids or blends thereof;
(e) N,N-dimethylamide of the formula $$RCON(CH_3)_2$$

wherein R is an alkyl chain derived from fatty acids having about 6 to about 18 carbon atoms; and (f) polybutenes of the following formula $$CH_3-\underset{CH_3}{\underset{|}{\overset{CH_3}{\overset{|}{C}}}}-\left[CH_2-\underset{CH_3}{\underset{|}{\overset{CH_3}{\overset{|}{C}}}}\right]_n-CH=C\overset{CH_3}{\underset{CH_3}{\diagdown}}$$

where n is a number from about 1 to about 50;

at least one surfactant selected from the group consisting of (a) fatty alkanolamides of the formula $$\underset{\diagdown R''}{\overset{O}{\overset{\|}{RCN}}\diagup R'}$$

wherein R is an alkyl group having from about 6 to about 25 carbon atoms; R' and R" are the same or different and are independently selected from the group consisting of hydrogen, —CH$_2$CH$_2$OH and $$-CH_2-\underset{CH_3}{\underset{|}{CH}}-OH$$

(b) PEG esters of the formula $$R^2\underset{O}{\overset{\|}{C}}-O(CH_2CH_2O)_mR^3$$

wherein $R^2$ is $C_2$–$C_{25}$ fatty alkyl having from about 2 to about 25 carbon atoms, $R^3$ is a fatty alkyl having from about 2 to about 25 carbon atoms or hydrogen and m is a number from 1 to about 100, (c) silicone surfactants of the formula $$CH_3-\underset{CH_3}{\underset{|}{\overset{CH_3}{\overset{|}{Si}}}}-O-\left[\underset{CH_3}{\underset{|}{\overset{CH_3}{\overset{|}{Si}}}}-O\right]_x-\left[\underset{\underset{O}{\underset{|}{(CH_2)_n}}}{\underset{|}{\overset{CH_3}{\overset{|}{Si}}}}-O\right]_y-\underset{CH_3}{\underset{|}{\overset{CH_3}{\overset{|}{Si}}}}-CH_3$$
$$(C_2H_4O)_a(C_3H_6O)_bR^6$$

wherein x is a number from 0 to about 5, y is a number from 1 to about 5, a is a number from about 3 to about 25, b is a number from 0 to about 25, n is a number from about 2 to about 4 and $R^6$ is hydrogen, an alkyl group having 1 to about 4 carbon atoms or an alkyl ester group having 1 to about 4 carbon atoms, (d) ethoxylated fatty acids $$R^7\overset{O}{\overset{\|}{C}}-O(CH_2CH_2O)_pH$$

wherein $R^7$ is an alkyl group having from about 6 to about 25 carbon atoms, p is a number from 1 to about 100, (e) alkyl ethoxylates $$R^8O(CH_2CH_2O)_qH$$

wherein $R^8$ is alkyl group having from 1 to about 50 carbon atoms and q is a number from 1 to about 100, (f) alkylphenol ethoxylates $$R^9-\underset{R^{10}}{\diagdown}\!\!\!\bigcirc\!\!\!-(OCH_2CH_2)_nOH$$

wherein $R^9$ is hydrogen or an alkyl having from about 1 to about 20 carbon atoms, $R^{10}$ is hydrogen or an alkyl having from about 1 to about 20 carbon atoms and n is a number from 1 to about 100, (g) polypropylene glycols $$HO-(\underset{CH_3}{\underset{|}{CH}}-CH_2-O)_{(t-1)}-CH_2-\underset{CH_3}{\underset{|}{\overset{CH_3}{\overset{|}{CH}}}}OH$$

wherein t is a number from 1 to about 100, (h) amine ethoxylates $$R^{11}-N\begin{matrix}(CH_2CH_2O)_gH\\ \\(CH_2CH_2O)_hH\end{matrix}$$

wherein g and h independently of one another are numbers from 1 to about 100 and R" is an alkyl having from 1 to about 25 carbon atoms and (i) tristyrylphenol alkoxylate, and a buffering agent is in an amount sufficient to reduce the pH to below about 7.

2. A composition as claimed in claim 1, wherein the buffering agent is selected from the group consisting of alkylaryl polyethoxy phosphate ester, $C_1$–$C_6$ carboxylic acids, $C_1$–$C_6$ dicarboxylic acids, phosphoric acid, citric acid, glutaric acid, gluconic acid, lactic acid, glycolic acid, acrylic acid, and carboxylated alcohol ethoxylate.

3. A composition according to claim 2, wherein the spray oil further comprises a paraffin oil having a distillation range of about 400° F. to about 450° F. at 10 mm Hg.

4. A composition according to claim 2, wherein the spray oil further comprises a paraffin oil having a distillation range of about 460° F. to about 470° F. at 10 mm Hg.

5. A composition according to claim 2, comprising 80 to 85% by weight spray oil and about 5 to about 20% by weight of the surfactant based on the total weight of the composition.

6. A composition as claimed in claim 5, wherein the buffering agent is about 0.5 to about 10% by weight based on the total weight of the composition.

7. A composition as claimed in claim 6, wherein the buffering agent to 0.5 to 5% by weight based on the total weight of the composition.

8. A composition according to claim 1, wherein the surfactant further comprises nonyl phenol ethoxylate.

9. A composition according to claim 8, wherein the nonyl phenol ethoxylate is in an amount of about 18%.

10. A composition according to claim 7, wherein the buffering agent is acetic acid.

11. A composition according to claim 7, wherein the buffering agent is propionic acid.

12. A composition according to claim 8, wherein the buffering agent is acetic acid.

13. A composition according to claim 8, wherein the buffering agent is a mixture of carboxylated alcohol ethoxylate and acetic acid.

14. A composition according to claim 1, wherein the surfactant consists of stearyl alcohol ethoxylate and the buffering agent is a mixture of acetic and lactic acid.

15. A composition according to claim 1, wherein the surfactant consists essentially of the mixture of nonyl phenol ethoxylate and a silicone surfactant.

16. A composition according to claim 15, wherein the buffering agent is a mixture of acetic acid and carboxylated alcohol ethoxylate.

17. A composition according to claim 1, wherein the surfactant is a mixture of nonyl phenol ethoxylate and PEG ester ethoxylate.

18. A composition according to claim 17, wherein the buffering agent is a mixture of acetic acid, citric acid, glutaric and carboxylated alcohol ethoxylate.

19. An insecticide comprising the adjuvant composition as claimed in claim 1.

20. A homogeneous, essentially nonaqueous adjuvant composition comprising at least one spray oil selected from the group consisting of
(a) vegetable oils;
(b) fatty acids and blends thereof;
(c) esterified fatty acids or blends thereof;
(d) saponified fatty acids or blends thereof;
(e) N,N-dimethylamide of the formula $$RCON(C_3)_2$$

wherein R is an alkyl chain derived from fatty acids having about 6 to about 18 carbon atoms;
(f) polybutenes of the following formula $$(CH_3)_3C-[C(C_3)_2CH_2]_n-CH=C(CH_3)_2$$

where n is a number from about 1 to about 50;
at least one surfactant selected from the group consisting of
(a) fatty alkanolamides of the formula $$RC\underset{\underset{O}{\parallel}}{N}\begin{matrix}R'\\ \\R''\end{matrix}$$

wherein R is a $C_6$–$C_{25}$ alkyl group; R' and R" are the same or different and are independently selected from the group consisting of hydrogen,

—$CH_2CH_2OH$ and

—$CH_2CH$—OH
       |
       $CH_3$ (b) PEG esters of the formula $$R^2C-O(CH_2CH_2O)_mR^3$$
$$\parallel$$
$$O$$

wherein $R^2$ is a fatty alkyl having from about 2 to about 25 carbon atoms, $R^3$ is a fatty alkyl having from about 2 to about 25 carbon atoms or hydrogen and m is a number from 1 to about 100, (c) silicone surfactants of the formula $$CH_3-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_x-\left[\underset{\underset{\underset{O}{|}}{\underset{(CH_2)_n}{|}}}{\overset{\overset{CH_3}{|}}{Si}}-O\right]_y-\underset{\underset{CH_3}{|}}{\overset{\overset{CH_3}{|}}{Si}}-CH_3$$

$$\qquad\qquad-(C_2H_4O)_a(C_3H_6O)_bR^6$$

wherein x is a number from 0 to about 5, y is a number from 1 to about 5, a is a number from about 3 to about 25, b is a number from 0 to about 25, n is a number from about 2 to about 4 and $R^6$ is a hydrogen, an alkyl group having 1 to about 4 carbon atoms or an alkyl ester group having 1 to 4 carbon atoms, (d) ethoxylated fatty acids $$R^7C-O(CH_2CH_2O)_pH$$
$$\parallel$$
$$O$$

wherein $R^7$ is an alkyl group having from about 6 to about 25 carbon atoms, p is a number from 1 to about 100, (e) alkyl ethoxylates $$R^8O(CH_2CH_2O)_qH$$

wherein R⁸ is alkyl group having from about 1 to about 50 carbon atoms and q is a number from 1 to about 100, (f) alkylphenol ethoxylates

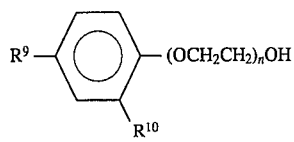

wherein R⁹ is hydrogen or an alkyl having from 1 to about 20 carbon atoms, R¹⁰ is hydrogen or an alkyl having from 1 to about 20 carbon atoms and n is a number from 1 to about 100, (g) polypropylene glycols $$HO-(CH-CH_2-O)_{(t-1)}-CH_2-CH-OH$$
$$\quad\quad |\quad\quad\quad\quad\quad\quad\quad\quad |$$
$$\quad CH_3\quad\quad\quad\quad\quad\quad\quad CH_3$$

wherein t is a number from 1 to about 100, (h) amine ethoxylates

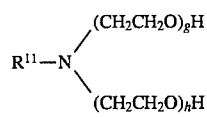

wherein g and h are numbers from 1 to about 100 and R¹¹ is an alkyl having from 1 to about 25 carbon atoms, and (i) tristyrylphenol alkoxylate and a buffering agent is in an amount sufficient to reduce the pH to below about 7, and wherein said surfactant is mixed with sorbitan fatty acid ester and/or a polyethoxylated derivative of a sorbitan fatty acid ester.

21. A homogeneous, essentially nonaqueous adjuvant composition comprising:
(1) at least one spray oil selected from the group consisting of:
(a) vegetable oils;
(b) fatty acids and blends thereof;
(c) esterified fatty acids or blends thereof;
(d) saponified fatty acids or blends thereof;
(e) N,N-dimethylamide of the formula

RCON(CH₃)₂ wherein R is an alkyl chain derived from fatty acids having about 6 to about 18 carbon atoms;
(f) polybutenes of the following formula

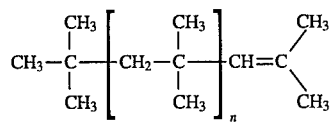

where n is a number from about 1 to about 50;
(2) a surfactant in an effective amount to provide emulsification of said composition and
(3) a buffering agent in an amount sufficient to reduce the pH to below 7.

22. The composition according to claim 21, wherein at least one of said spray oil is selected from the group consisting of:
(b) fatty acids and blends thereof;
(c) esterified fatty acids or blends thereof;
(d) saponified fatty acids or blends thereof;
(e) N,N-dimethylamide of the formula

RCON(CH₃)₂ wherein R is an alkyl chain derived from fatty acids having about 6 to about 18 carbon atoms; and
(f) polybutenes of the following formula

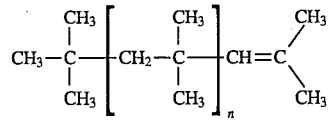

where n is a number from about 1 to about 50;
a surfactant in an effective amount to provide a emulsification of said composition and a buffering agent in an amount sufficient to reduce the pH below about 7.

23. The composition according to claim 21, wherein said spray oil contains vegetable oils and said vegetable oils are cotton seed oil, canola, rapeseed, peanut oil, sunflower oil, linseed oil, safflower oil, soybean oil, corn oil, olive oil, coconut oil, or tall oil, or mixtures thereof.

24. The composition according to claim 21, wherein said spray oil contains fatty acids and blends thereof and said fatty acids and blends thereof are saturated and unsaturated fatty acids of about 6 to about 18 carbon atoms.

25. The composition according to claim 21, wherein said spray oil contains said esterified fatty acids or blends thereof and said esterified fatty acids or blends thereof are saturated and unsaturated esters of about 6 to about 18 carbon atoms.

26. The composition according to claim 21, wherein said spray oil contains said saponified fatty acids or blends thereof and saponified fatty acids or blends thereof are saturated and unsaturated soaps of about 6 to about 18 carbon atoms.

27. The composition according to claim 24, wherein said spray oil contains a vegetable oil in an amount of about 50% to about 99% and the surfactant is a silicone surfactant in an amount of about 5 to about 19.5%.

28. The composition according to claim 21, wherein said spray oil contains fatty acids in an amount of about 50%.

29. A homogeneous, essentially nonaqueous adjuvant composition comprising a spray oil having a minimum of 85% of unsulfonated residue value, at least one surfactant selected from the group consisting of
(a) fatty alkanolamides of the formula

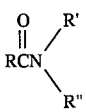

wherein R is a C₆–C₂₅ alkyl group; R and R" are the same or different and are independently selected from the group consisting of hydrogen, —CH₂CH₂OH and —CH₂—CH—OH,

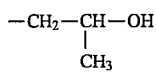

(b) PEG esters of the formula

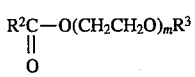

wherein R² is a C₂–C₂₅ fatty alkyl, R³ is a C₂–C₂₅ fatty alkyl or hydrogen and m is a number from 1 to 100, (c) silicone surfactants of the formula

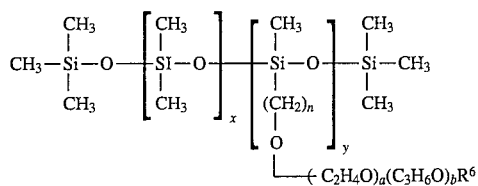

wherein x is a number from 0 to 5, y is a number from 1 to 5, a is a number from 3 to 25, b is a number from 0 to 25, n is a number from 2 to 4 and $R^6$ is hydrogen, an alkyl group having 1 to 4 carbon atoms or an alkyl ester group having 1 to 4 carbon atoms, (d) ethoxylated fatty acids

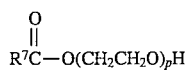

wherein $R^7$ is a $C_6$–$C_{25}$ alkyl group, p is a number from 1 to 100, (e) alkyl ethoxylates

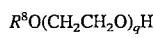

wherein $R^7$ is alkyl group and q is a number from 1 to 100, (f) alkylphenol ethoxylates

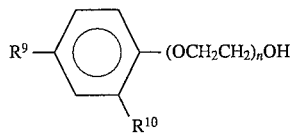

wherein $R^9$ is hydrogen or $C_1$–$C_{20}$ alkyl, $R^{10}$ is hydrogen or $C_1$–$C_{20}$ alkyl and n is a number from 1 to 100, (g) polypropylene glycols

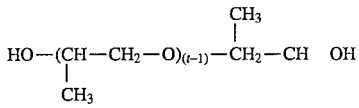

wherein t is a number from 1 to 100, (h) amine ethoxylates

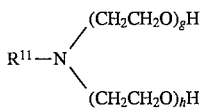

wherein g and h are numbers from 1 to 100 and R" is a $C_1$–$C_{25}$ alkyl and (i) tristyrylphenol alkoxylate, and a buffering agent in an amount sufficient to reduce the pH to below 7.

30. The composition as claimed in claim 29, wherein said surfactant is mixed with sorbitan fatty acid ester and/or a polyethoxylated derivative of a sorbitan fatty acid ester.

* * * * *